US006921192B2

(12) United States Patent
Vendrely et al.

(10) Patent No.: US 6,921,192 B2
(45) Date of Patent: Jul. 26, 2005

(54) BONE CEMENT MIXING APPARATUS (75) Inventors: Timothy G. Vendrely, Warsaw, IN (US); Samuel G. Sackett, Ft. Wayne, IN (US); Leslie J. Ungers, Cincinnati, OH (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 264 days.

(21) Appl. No.: 10/112,016

(22) Filed: Mar. 29, 2002

(65) Prior Publication Data

US 2003/0185093 A1 Oct. 2, 2003

(51) Int. Cl.⁷ .................................................. B01F 13/06
(52) U.S. Cl. ........................ 366/139; 366/252; 220/661; 220/756
(58) Field of Search ................................. 366/139, 247, 366/252, 64, 65, 67, 75, 129, 130; 422/224, 225; 220/366.1, 745, 756, 661, 676, 913

(56) References Cited

U.S. PATENT DOCUMENTS

| 215,850 | A | 5/1879 | Whelchel |
|---|---|---|---|
| 261,425 | A | 7/1882 | Blair |
| 341,306 | A | 5/1886 | Allen |
| 347,916 | A | 8/1886 | Bogart |
| 409,533 | A | 8/1889 | Walter |
| 642,650 | A | 2/1900 | Walker et al. |
| 856,295 | A | 6/1907 | Prindle |
| 1,101,199 | A | 6/1914 | Legg et al. |
| 1,459,148 | A | 6/1923 | Flynt |
| 1,698,402 | A | 1/1929 | Harris |
| 2,150,888 | A | 3/1939 | Barnard |
| 2,269,736 | A | 1/1942 | Rogers |
| 2,305,238 | A | 12/1942 | Coates |
| 2,561,203 | A | 7/1951 | Joffe |
| 2,570,126 | A | 10/1951 | Hobbs |
| 2,572,375 | A | 10/1951 | Oertli |
| 2,696,022 | A | 12/1954 | Steinbock et al. |
| 2,732,102 | A | 1/1956 | Ekins |
| 2,750,943 | A | 6/1956 | Dann |
| 2,898,094 | A | 8/1959 | O'Neill, Jr. |
| 3,029,653 | A | 4/1962 | Nilsson |
| 3,053,457 | A | 9/1962 | Trumbull et al. |
| 3,141,583 | A | 7/1964 | Mapel et al. |
| 3,169,156 | A | 2/1965 | Johnson et al. |
| 3,193,146 | A | 7/1965 | Isgriggs et al. |
| 3,255,747 | A | 6/1966 | Cochran et al. |
| 3,640,510 | A | 2/1972 | Lea |
| 3,704,007 | A | 11/1972 | Kroeger |
| 3,894,663 | A | 7/1975 | Carhart et al. |
| 4,015,945 | A | 4/1977 | Frankel et al. |
| 4,079,917 | A | 3/1978 | Popeil |

(Continued)

FOREIGN PATENT DOCUMENTS

| DE | 29 21 565 | 12/1980 |
|---|---|---|
| DE | 195 32 015 A1 | 3/1997 |
| EP | 0 616 552 B1 | 9/1994 |

(Continued)

OTHER PUBLICATIONS

DePuy Orthopaedics, Inc. Prism Vacuum Mixing Bowl, © 2001. Single Page Brochure.
DePuy Orthopaedics, Inc. Vacuum Mixing System. © 2000. Single Page Brochure.

*Primary Examiner*—David Sorkin
(74) *Attorney, Agent, or Firm*—Maginot Moore & Beck (57) ABSTRACT

A bone cement mixing apparatus includes a bowl, an attachable/detachable lid, and a handle extending from the bowl. The bowl incorporates a bone cement vapor removal system that allows the extraction of bone cement vapors or fumes even after the lid has been detached from the bowl. Such extraction of vapors may be continuous. The vapor removal system is coupled to a vacuum source. The handle is ergonomically shaped and incorporates vacuum tubing that couples the bone cement vapor removal system of the bowl with the vacuum source.

22 Claims, 9 Drawing Sheets

U.S. PATENT DOCUMENTS

| | | |
|---|---|---|
| 4,090,639 A | 5/1978 | Campbell et al. |
| 4,149,455 A | 4/1979 | Ross |
| 4,185,072 A | 1/1980 | Puderbaugh et al. |
| 4,277,184 A | 7/1981 | Solomon |
| 4,338,925 A | 7/1982 | Miller |
| 4,339,058 A | 7/1982 | Wendt |
| 4,342,310 A | 8/1982 | Lindmayer et al. |
| 4,356,938 A | 11/1982 | Kayser |
| 4,364,388 A | 12/1982 | Cech |
| 4,406,654 A | 9/1983 | Bristow |
| 4,425,121 A | 1/1984 | Young et al. |
| 4,460,279 A | 7/1984 | Krasney |
| 4,488,817 A | 12/1984 | Uesaka et al. |
| 4,546,767 A | 10/1985 | Smith |
| 4,569,662 A | 2/1986 | Dragan |
| 4,576,152 A | 3/1986 | Müller et al. |
| 4,619,613 A | 10/1986 | Dragan |
| 4,671,263 A | 6/1987 | Draenert |
| 4,721,390 A | 1/1988 | Lidgren |
| 4,738,664 A | 4/1988 | Prindle |
| 4,758,096 A | 7/1988 | Gunnarsson |
| 4,768,955 A | 9/1988 | Hirdes |
| 4,787,751 A | 11/1988 | Bakels |
| 4,787,893 A | 11/1988 | Villette |
| 4,854,716 A | 8/1989 | Ziemann et al. |
| 4,861,339 A | 8/1989 | Jonischkeit |
| 4,940,294 A | 7/1990 | Foster |
| 4,961,647 A | 10/1990 | Coutts et al. |
| 4,966,601 A | 10/1990 | Draenert |
| 4,973,168 A | 11/1990 | Chan |
| 4,973,334 A | 11/1990 | Ziemann |
| 4,994,065 A | 2/1991 | Gibbs et al. |
| 5,022,563 A | 6/1991 | Marchitto et al. |
| 5,073,033 A | 12/1991 | Klepeis |
| 5,090,816 A | 2/1992 | Socha |
| 5,094,543 A | 3/1992 | Mursa |
| 5,100,241 A | 3/1992 | Chan |
| 5,125,836 A | 6/1992 | Dragan et al. |
| 5,145,250 A | 9/1992 | Planck et al. |
| 5,152,432 A | 10/1992 | De Laforcade |
| 5,193,907 A | 3/1993 | Faccioli et al. |
| 5,197,635 A | 3/1993 | Chang |
| 5,199,788 A | 4/1993 | Stallings |
| 5,252,301 A | 10/1993 | Nilson et al. |
| 5,265,956 A | 11/1993 | Nelson et al. |
| 5,289,731 A | 3/1994 | Womack |
| 5,304,147 A | 4/1994 | Johnson et al. |
| 5,328,262 A | 7/1994 | Lidgren et al. |
| 5,335,824 A | 8/1994 | Weinstein |
| 5,344,232 A | 9/1994 | Nelson et al. |
| 5,348,391 A | 9/1994 | Murray |
| 5,368,386 A | 11/1994 | Murray |
| 5,374,121 A | 12/1994 | Draenert |
| 5,381,931 A | 1/1995 | Chang |
| 5,395,167 A | 3/1995 | Murray |
| 5,415,474 A | 5/1995 | Nelson et al. |
| 5,431,654 A | 7/1995 | Nic |
| 5,432,645 A | 7/1995 | Terunuma et al. |
| 5,435,645 A | 7/1995 | Faccioli et al. |
| 5,443,182 A | 8/1995 | Tanaka et al. |
| 5,472,445 A | 12/1995 | Yakimicki et al. |
| 5,494,349 A | 2/1996 | Seddon |
| 5,501,520 A | 3/1996 | Lidgren et al. |
| 5,505,538 A | 4/1996 | Earle |
| 5,509,578 A | 4/1996 | Livingstone |
| RE35,276 E | 6/1996 | Chan |
| 5,545,460 A | 8/1996 | Tanaka et al. |
| 5,549,381 A | 8/1996 | Hays et al. |
| 5,551,778 A | 9/1996 | Hauke et al. |
| 5,558,136 A | 9/1996 | Orrico |
| 5,571,282 A | 11/1996 | Earle |
| 5,586,821 A | 12/1996 | Bonitati et al. |
| 5,588,745 A | 12/1996 | Tanaka et al. |
| 5,624,184 A | 4/1997 | Chan |
| 5,638,997 A | 6/1997 | Hawkins et al. |
| 5,797,678 A | 8/1998 | Murray |
| 5,797,679 A | 8/1998 | Grulke et al. |
| 5,842,786 A | 12/1998 | Solomon |
| 5,875,928 A | 3/1999 | Muller et al. |
| 5,934,803 A | 8/1999 | Hutter |
| 5,961,211 A | 10/1999 | Barker et al. |
| 5,975,751 A | 11/1999 | Earle |
| 6,024,480 A | 2/2000 | Seaton et al. |
| 6,033,105 A | 3/2000 | Barker et al. |
| 6,042,262 A | 3/2000 | Hajianpour |
| 6,193,108 B1 | 2/2001 | Lepsius et al. |
| 6,224,253 B1 | 5/2001 | Dixon |
| 6,254,268 B1 | 7/2001 | Long |
| 6,296,141 B1 | 10/2001 | Lukacevic |
| 6,296,149 B1 | 10/2001 | Long |
| 6,435,705 B1 * | 8/2002 | Long .................... 366/139 |
| 6,536,937 B1 * | 3/2003 | Burchett ............... 366/139 |
| 2002/0067657 A1 * | 6/2002 | Vendrely et al. ...... 366/139 |
| 2002/0067658 A1 * | 6/2002 | Vendrely et al. ...... 366/139 |

FOREIGN PATENT DOCUMENTS

| | | |
|---|---|---|
| EP | 1 068 893 A2 | 1/2001 |
| FR | 86 06781 | 4/1986 |
| GB | 178572 | 4/1922 |
| GB | 517340 | 1/1940 |
| GB | 2187110 | 9/1987 |
| GB | 2 276 560 | 4/1992 |
| WO | WO 84/03830 | 10/1984 |
| WO | WO 88/08327 | 11/1988 |
| WO | WO 89/01322 | 2/1989 |
| WO | WO 93/10892 | 6/1993 |
| WO | WO 99/06140 | 2/1999 |

* cited by examiner

BONE CEMENT MIXING APPARATUS

CROSS REFERENCE

Cross reference is made to copending U.S. utility patent application Ser. No. 10/002,045 filed Nov. 15, 2001, entitled "Bone Cement Mixing Apparatus Having Improved Gearing Arrangement for Driving a Mixing Blade" by Timothy G. Vendrely, Jack F. Long, Christopher Battles, Paul DeCesare, Patrick Gutelius, and Samuel G. Sackett which is assigned to the same assignee as the present invention. The disclosure of the above-identified U.S. utility patent application is hereby totally incorporated by reference herein in its entirety.

Cross reference is also made to copending U.S. utility patent application Ser. No. 10/002,729 filed Nov. 15, 2001, entitled "Bone Cement Mixing Apparatus Having Improved Blade Configuration" by Timothy G. Vendrely, and Samuel G. Sackett which is assigned to the same assignee as the present invention. The disclosure of the above-identified U.S. utility patent application is hereby totally incorporated by reference herein in its entirety.

TECHNICAL FIELD OF THE INVENTION

The present invention relates generally to a surgical assembly and, more particularly, to an apparatus and method for mixing bone cement.

BACKGROUND OF THE INVENTION

It is necessary in many orthopedic surgical procedures to employ a cement or grouting type agent, such as for attaching artificial joint implants, repairing or forming joints in bones, or other forms of orthopedic work. The type of cement generally used for these purposes is a self-curing resin formed from the blending of a wide variety of liquid monomers or comonomers with powdered polymers or copolymers to form a viscous admixture to be used as the grouting agent.

The admixture of the powder and liquid components develops a quick setting material. As such, preparation of the cement usually occurs directly within the operating area just prior to use. In particular, a bone cement mixing apparatus is generally utilized to mix the powder and liquid components in the operating area. The resultant admixture is then removed from the mixing apparatus and placed in a cement delivery apparatus for subsequent use by the surgeon. Specifically, the bone cement must generally first be scooped or otherwise removed from the mixing apparatus and thereafter placed in a syringe-type delivery apparatus for use by the surgeon.

The aforedescribed system for mixing and delivering bone cement has a number of drawbacks associated therewith. For example, monomer vapors are generated during the depositing of the monomer into the mixing apparatus and during the subsequent mixing of the monomer with the powder component of the bone cement. Such monomer vapors may be noxious and/or toxic. Because the bone cement is generally mixed in an operating room environment, it is important to prevent any monomer or its vapors from escaping the mixing apparatus. Because of this, some heretofore designed mixing apparatus have included mechanisms for controlling the escape of such vapors.

Such heretofore mixing apparatus can be categorized into three main mixing bowl systems. These three main mixing bowl systems are currently used in the industry. Once such mixing bowl is known as the Stryker mixing bowl. The Stryker mixing bowl utilizes a vacuum during the mixing process to remove fumes. The Stryker mixing bowl, however, has several deficiencies. Such deficiencies are that the mixing bowl is not clear so that the mix quality cannot be visualized, it has a fixed axis direct drive paddle that may allow for un-mixed powder to collect near the top of the bowl, and the lid does not lock into place. The direct drive paddle means that the user must manually reverse direction of the paddle to obtain the optimal mix quality of the cement. Further, the Stryker mixing bowl, while using a vacuum to remove monomer fumes during mixing, cannot remove the monomer fumes once the lid is removed.

Another type of mixing bowl is known as the Summit Prism mixing bowl. The Summit Prism mixing bowl has a gearing mechanism that creates a spirograph-type pattern within the cement being mixed. This action combined with the design of the paddle creates a folding motion of the cement which has been seen to mix cement fairly well. The paddle does not, however, reverse its direction. The paddle does, however, create a taffy pulling motion within the cement being mixed. The lid to the Summit Prism mixing bowl does lock, and the mixing bowl is clear to provide visualization of the mix quality of the cement. the Summit Prism mixing bowl, however, is not ergonomically designed and thus is hard to hold. Again, while using a vacuum to remove monomer fumes during mixing, the Summit Prism mixing bowl suffers from the same limitation as the Stryker mixing bowl in that there is no provision for removal of the monomer fumes once the lid is removed.

The third major system is the UltraMix mixing bowl made by DePuy Orthopaedics, Inc. of Warsaw, Ind. The UltraMix mixing bowl has an ergonomic sauce-pan type handle on the lid, the lid locks into place, and the blow interfaces with the DePuy Monomer Introducer also made by DePuy Orthopaedics, Inc. of Warsaw, Ind. The paddle of the Ultra-Mix mixing bowl is a direct drive system, but is offset thus creating the folding motion within the cement being mixed that is advantageous. The direct drive paddle means that to obtain the optimal mix quality of the cement, the paddle needs to be reversed. As well, the speed of the paddle needs to be varied. Again, while using a vacuum to remove monomer fumes during mixing, the UltraMix mixing bowl suffers from the same limitation as the Stryker and Summit Prism mixing bowls, in that there is no provision for removal of the monomer fumes once the lid is removed.

In all heretofore systems, and not just the ones mentioned above, there is no means for actively removing monomer fumes once the mixing bowl lid is removed. Since such monomer fumes/vapors may be noxious and/or toxic, it is important to remove as much of the vapors as possible. With some cements, it is necessary to wait up to four minutes before the cement is ready for use.

Moreover, heretofore designed mixing apparatus have been plagued with problems relating to the incomplete mixing of the liquid component with the powder component. Specifically, the powder component and liquid component are often inadequately mixed during operation of heretofore designed systems.

What is therefore needed is an apparatus and/or method for mixing a bone cement that overcomes one or more of the above-mentioned drawbacks or inadequacies. What is particularly needed is an apparatus and/or method for mixing bone cement that reduces, if not eliminates, exposure to vapors form the liquid bone cement component within the operating area.

SUMMARY OF THE INVENTION

In accordance with the concepts of the subject invention, there is provided a bone cement mixing device having a bowl that incorporates vacuum assisted bone cement vapor removal. The bone cement mixing device allows bone cement fumes or vapors to be removed even when the lid has been detached. Particularly, the subject invention provides a bone cement mixing apparatus that includes a bowl, an attachable/detachable lid, and a handle extending from the bowl. The bowl incorporates a bone cement vapor removal system that allows the extraction of bone cement vapors or fumes even after the lid has been detached from the bowl.

In one form, the subject invention provides a bone cement mixing apparatus. The bone cement mixing apparatus includes a bowl defining an interior, a lid detachably attachable to the bowl, and a bone cement vapor removal system formed in the bowl and operative to allow extraction of bone cement vapors or fumes from the interior.

In another form, the subject invention provides a bone cement mixing system. The bone cement mixing system includes a bowl defining an interior, an annular chamber formed in an upper annular rim of the bowl, a plurality of inlet ports formed in the upper annular rim and providing communication between the interior of the bowl and the chamber, a lid detachably attachable to the upper rim of the bowl, an annular seal disposed on the upper rim; and an outlet port in communication with the chamber and configured to be coupled to a vacuum source.

In yet another form, the subject invention provides a bone cement mixing system including a mixing bowl device and a vacuum source. The mixing bowl device includes a bowl defining an interior, a lid detachably attachable to the bowl, and a bone cement vapor removal system formed in the bowl and operative to allow extraction of bone cement vapors or fumes from the interior when in communication with the vacuum source.

In still another form, there is provided a method of mixing bone cement. The method includes the steps of: (a) introducing bone cement components into a bone cement mixing bowl device, the bone cement mixing bowl device a bowl defining an interior, a lid detachably attachable to the bowl, and a bone cement vapor removal system formed in the bowl including an outlet port in communication with the bone cement vapor removal system, (b) connecting the outlet port to a vacuum source, and (c) turning on the vacuum source.

According to an aspect of the subject invention, the inlet ports are distributed along an upper, interior rim of the bowl. In one form, each inlet port is the same size. Alternatively, the inlet ports may be variable in size depending on position on the interior rim and/or distance from the outlet port. In one form, a first set of inlet ports of a first size are situated proximate or close to the outlet port, while a second set of inlet ports of a second size that is greater or larger than the first size are situated distal or away from the outlet port. In another form, the inlet ports are graduated in variability from proximate the outlet port to distal the outlet port, such as inlet ports that continuously increase in size, or as inlet ports that continuously decrease in size.

It is therefore an object of the subject invention to provide a new and useful apparatus for mixing bone cement.

It is moreover an object of the subject invention to provide an improved apparatus for mixing bone cement.

It is further an object of the subject invention to provide a new and useful method for mixing bone cement.

It is also an object of the subject invention to provide an improved method for mixing bone cement.

It is yet another object of the subject invention to provide an apparatus and/or method for mixing bone cement that reduces, if not eliminates, exposure to vapors from the liquid bone cement component within an operating area.

The above and other objects, features, and/or advantages of the subject invention will become apparent from the following description and the attached drawings.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention.

Figure 1:
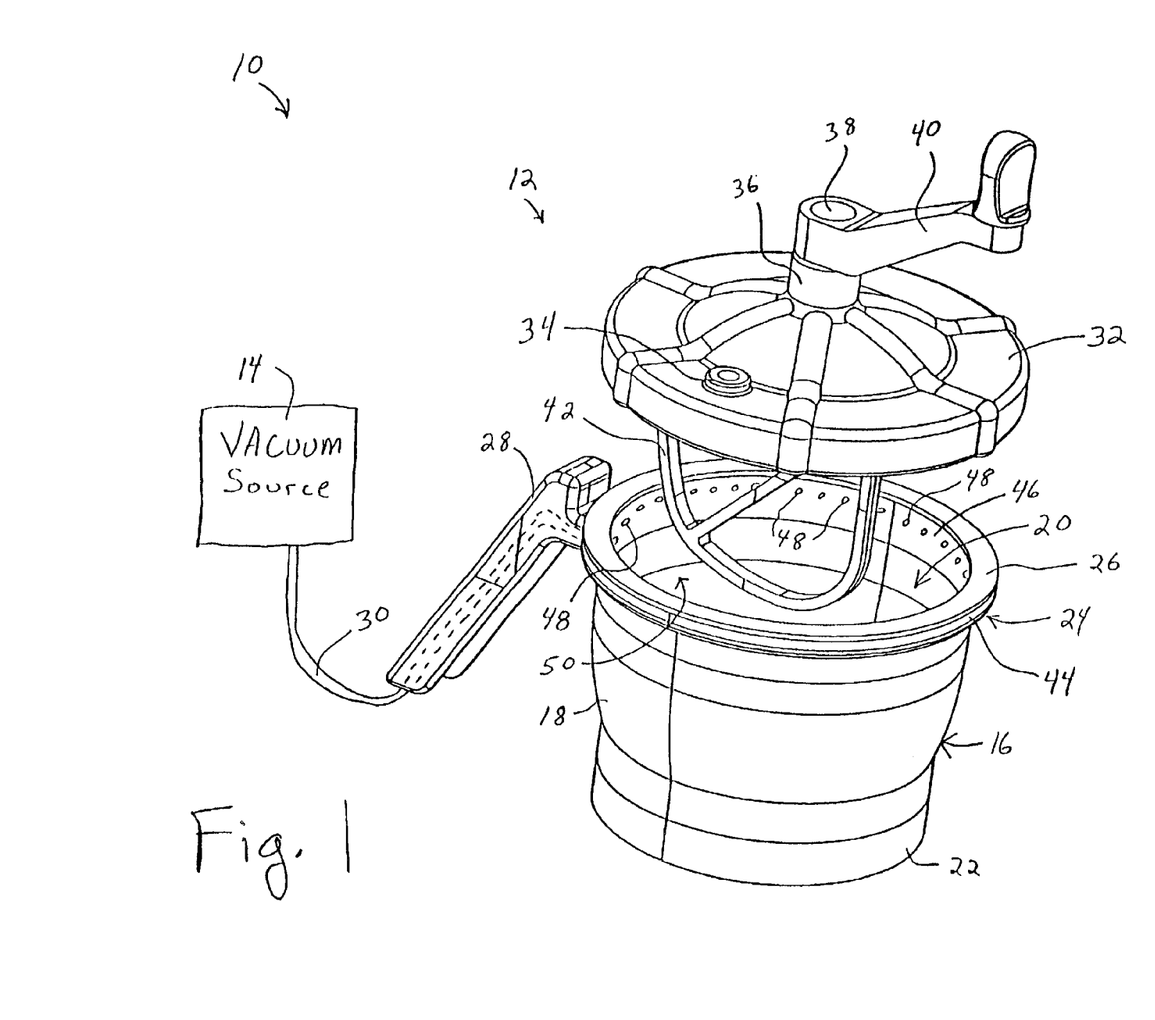
FIG. 1 is a first perspective view of an exemplary bone cement mixing system including an exemplary bone cement mixing apparatus in accordance with the principles of the subject invention, the exemplary bone cement mixing apparatus having its lid or cover removed and coupled to a vacuum source.
Figure 2:
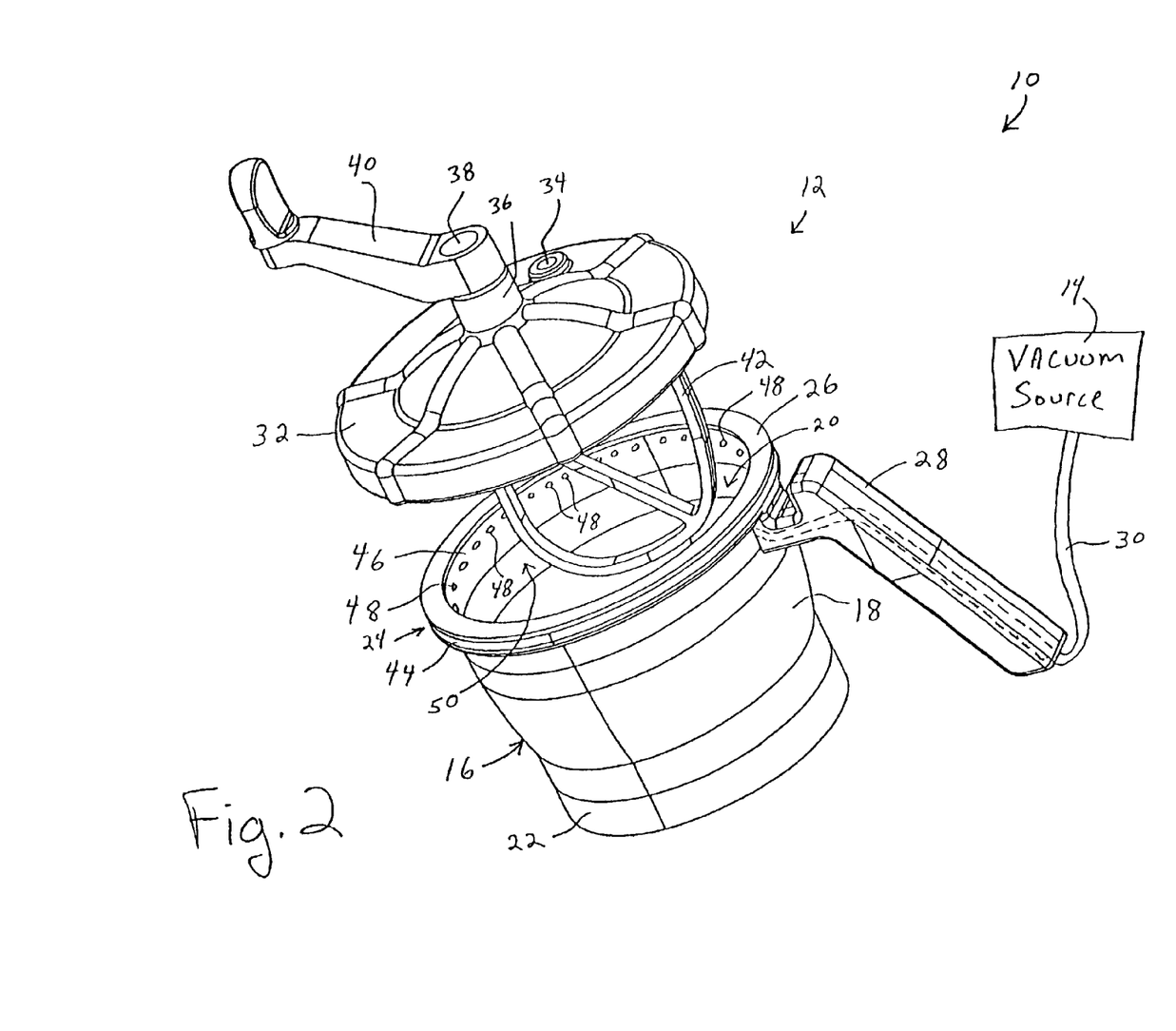
FIG. 2 is a second perspective view of the exemplary bone cement mixing system including the exemplary bone cement mixing apparatus in accordance with the principles of the subject invention, the exemplary bone cement mixing apparatus having its lid or cover removed and coupled to the vacuum source.

Referring now to FIGS. 1 and 2 there is shown an exemplary embodiment of a bone cement mixing system generally designated 10. The bone cement mixing system 10 includes an exemplary bone cement mixing apparatus, generally designated 12, in communication with a vacuum source, generally designated 14, via tubing 30 or the like. The vacuum source 14 may be any vacuum source that provides a vacuum, such as an UltraMix Foot-Pump offered by DePuy Orthopedics, Inc. of Warsaw, Ind., manual or automatic vacuum pump, or the like. The vacuum source may be controllable both as to intermittent or continuous use and as to vacuum pressure, but not necessarily. In all cases, the vacuum source is operative to pull a vacuum. The vacuum source 14 may also include a fume or vapor filter and/or storage device that allows the entrapment and/or accumulation of vapors coming therein.

The bone cement mixing apparatus 12 includes a bowl 16 defined by a body 18. The body 18 is preferably clear and/or translucent and made from a suitable plastic although other non-clear and/or non-translucent materials may be used. The body 18 is generally cylindrical and defines an interior, chamber, cavity or the like 20. The cavity 20 is where bone cement is mixed. Particularly, the cavity 20 is where the monomer is received and mixed.

The body 18 has a bottom rim 22 that allows the bowl 16 to stand upright when placed on a surface. Additionally, the body 18 has an upper rim structure 24 on which is supported a seal, gasket, or the like 26. The rim structure 24 and thus the seal 26 is substantially ring-shaped. The seal 26 is removably situated on and/or over the rim structure 24.

A handle 28 extends from the body 18 and is preferably formed integral therewith. The handle 28 is ergonomically shaped. Particularly, the handle 28 is styled in a sauce-pan type configuration that allows a user to easily grasp the handle 28 and thus move the bowl 16. The handle 28 is canted at an angle from the body 18. Particularly, the handle 28 is angled away from a vertical defined by the body 18 and/or rim structure 24. The handle 28 holds or retains the tubing 30, or alternatively, the tubing 30 extends through the handle 28. The tubing 30 provides communication between the vacuum source 14 and a bone cement vapor removal system, feature, structure, or the like generally designated 50. The bone cement vapor removal system 50 will be described in greater detail below.

The bone cement mixing apparatus 12 further includes a lid 32 that is configured, adapted, and/or operative to releasably lock with the bowl 16. Particularly, the lid 32 is releasably lockable onto the rim structure 24. In so doing, the seal 26 is compressed onto the rim structure 24. The lid 32 is preferably clear and/or translucent and made from a suitable plastic although other non-clear and/or non-translucent materials may be used.

The lid 32 has a monomer inlet, bore, hole or the like 34 that provides selective communication between outside of the lid 32 and inside of the lid 32, wherein inside of the lid 32 equates to the cavity 20 of the bowl 16. The inlet 34 is preferably configured, adapted, and/or operative to coupled to, receive, and/or interface with a monomer introducer (a monomer holder) such as the DePuy Monomer Introducer the subject of U.S. Pat. No. 6,296,149.

The lid 32 has a hole (not specifically seen in the figures) that is preferably positioned centrally, but not necessarily, in the lid 32. A collar 36 is disposed on the lid 32 over the hole. The collar 36 has a bore that corresponds with the hole in the lid 32. A rotatable shaft 38 extends through the bore of the collar 36 and through a hole on one end of a crank 40. The shaft 38 rotatably supports the crank 40. Rotation of the crank 40 rotates the shaft 38. As explained below, rotating the crank 40 moves a mixing blade 42. The mixing blade 42 is paddle-shaped to provide adequate mixing of the monomers introduced into the interior 20. A detailed explanation of the present mixing blade 42 is provided in U.S. patent application Ser. No. 10/002,729 previously incorporated herein by reference. Reference should be made thereto for further explanation of the mixing blade 42.

The rim structure 24, at the top of the bowl 16, defines an outer wall 44 and an inner wall 46. The outer and inner walls 44 and 46 oppose each other and are essentially annular or ring-shaped. The outer and inner walls 44 and 46 are spaced from each other. The seal 26 is sized to extend from the outer wall 44 to the inner wall 46 and thus cover the gap or space therebetween. The inner wall 46 has a plurality of holes, bores, openings, inlets, ports, or the like 48 formed therein. Particularly, the ports 48 are formed about the inner periphery of the rim structure 24 in the inner wall 46. The ports 48 preferably extend about the entire inner periphery, but not necessarily. The number of ports 48 is variable as well as the particular size. The ports 48 may be uniform in size or may be variable in size. In all cases, the ports 48 are configured, adapted and/or operative to allow fumes and/or vapors within the interior 20 to pass therethrough. It should also be appreciated that rather than a plurality of ports, there may be only one port.

Figure 8:
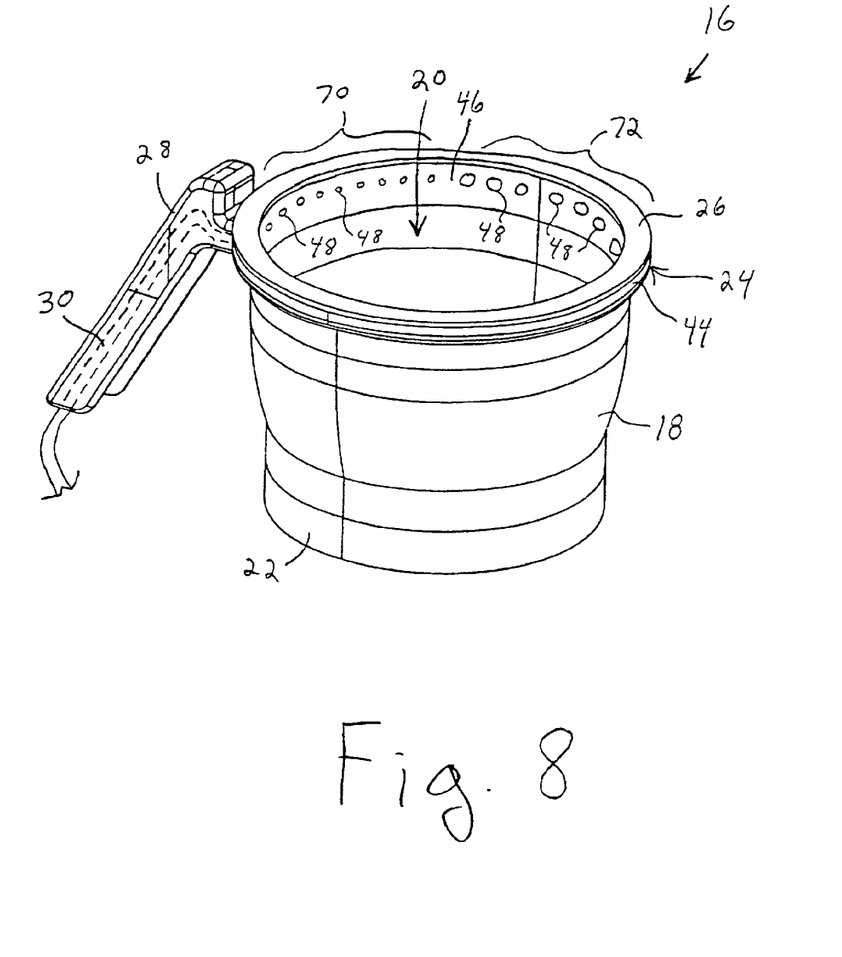
FIG. 8 is a perspective view of the bowl depicting an alternative embodiment of inlet ports.

Referring to FIG. 8, there is depicted an alternative form of the inlet ports 48 that are distributed along the upper, interior of the bowl 16. Rather than inlet ports 48 of uniform size, the inlet ports 48 may be variable in size depending on position on the interior rim and/or distance from the outlet port. As depicted in FIG. 8, a first set 70 of inlet ports 48 of a first size are situated proximate or close to the outlet port, while a second set 72 of inlet ports 48 of a second size that is greater or larger than the first size are situated distal or away from the outlet port. Of course, other variations, such as a plurality of sets of inlet ports 48 of various sizes increasing or decreasing from the outlet port, wherever situated, to distal thereof are contemplated.

Figure 9:
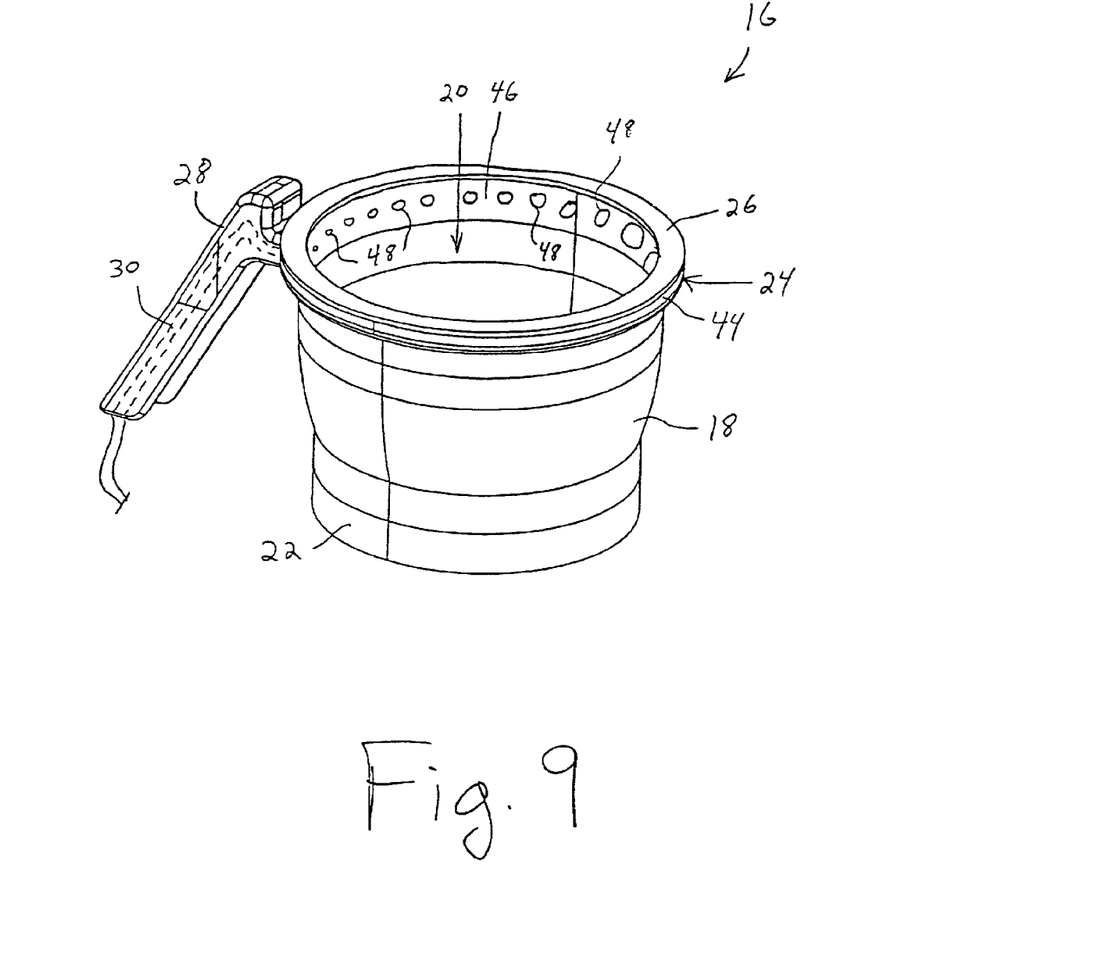
FIG. 9 is a perspective view of the bowl depicting another alternative embodiment of inlet ports.

Referring to FIG. 9, there is depicted an alternative form of the inlet ports 48 that are distributed along the upper, interior of the bowl 16. Rather than inlet ports 48 of uniform size or sets or various sizes, each inlet port 48 may be variable in size in relation to the other inlet ports 48 depending on position on the interior rim and/or distance from the outlet port. As depicted in FIG. 9, the inlet ports 48 are graduated in size from proximate the outlet port to distal the outlet port, such as inlet ports 48 that continuously increase in size as shown. Of course, other variations, such as inlet ports 48 that continuously decrease in size from the outlet port, wherever situated, to distal thereof, are contemplated.

These alternative embodiments may achieve a greater uniform airflow across the top of the bowl 16, particularly when the lid 32 is removed. Since air will tend to find the route of least resistance, providing inlet ports 48 that are smaller near (proximate) the outlet port 31 (see FIG. 7), provides a greater resistance to air flow, while providing inlet ports 48 that are larger at the opposite side of the outlet port 31 (away or distal), provides less resistance to air flow. In this manner volumetric air flow may be more evenly distributed across the top of the bowl 16 and thus improve vapor removal efficiency, both when the lid 32 is on and off.

Figure 5:
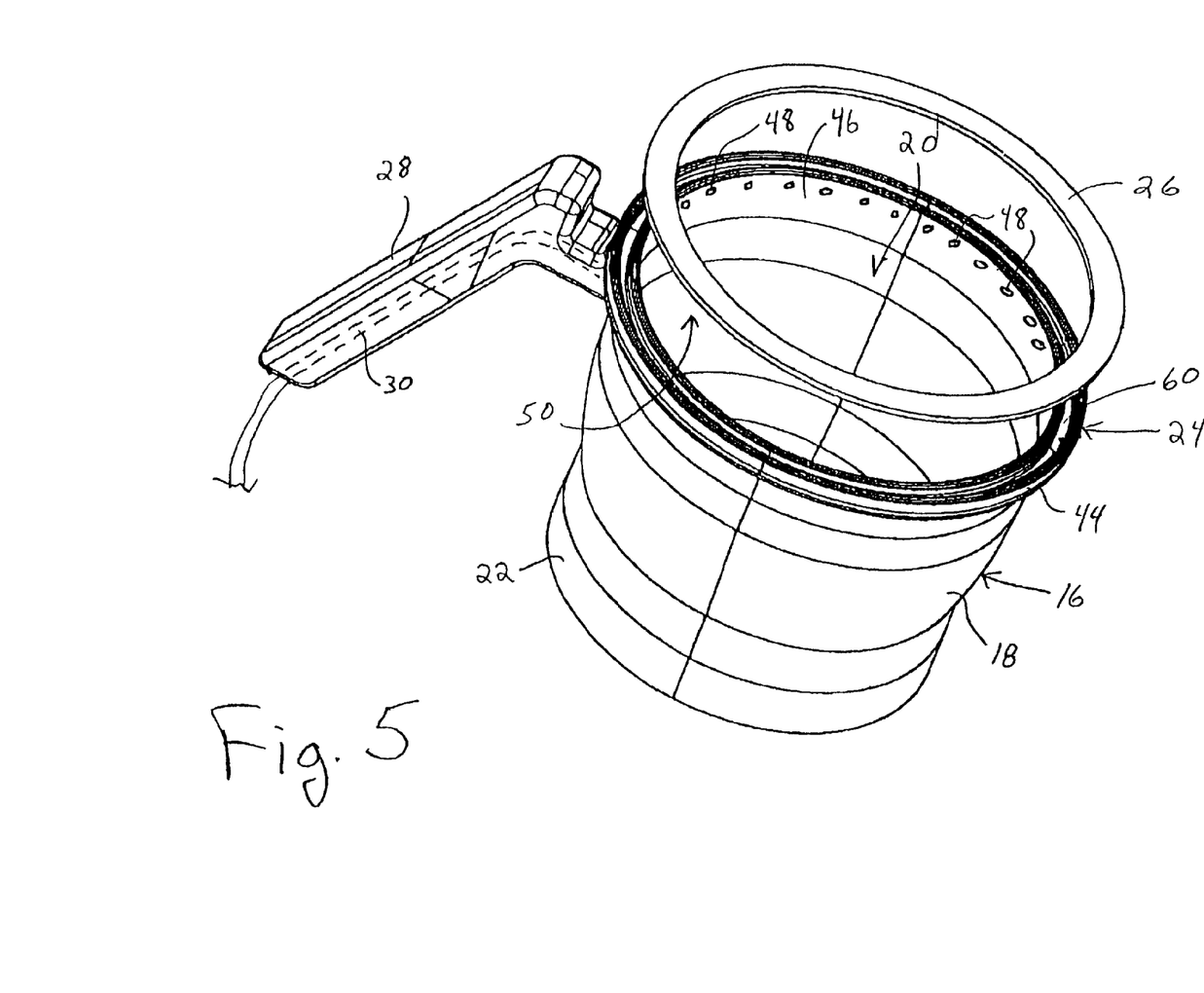
FIG. 5 is a perspective view of the bowl and vacuum seal in an exploded view therefrom of the exemplary bone cement mixing apparatus.
Figure 6:
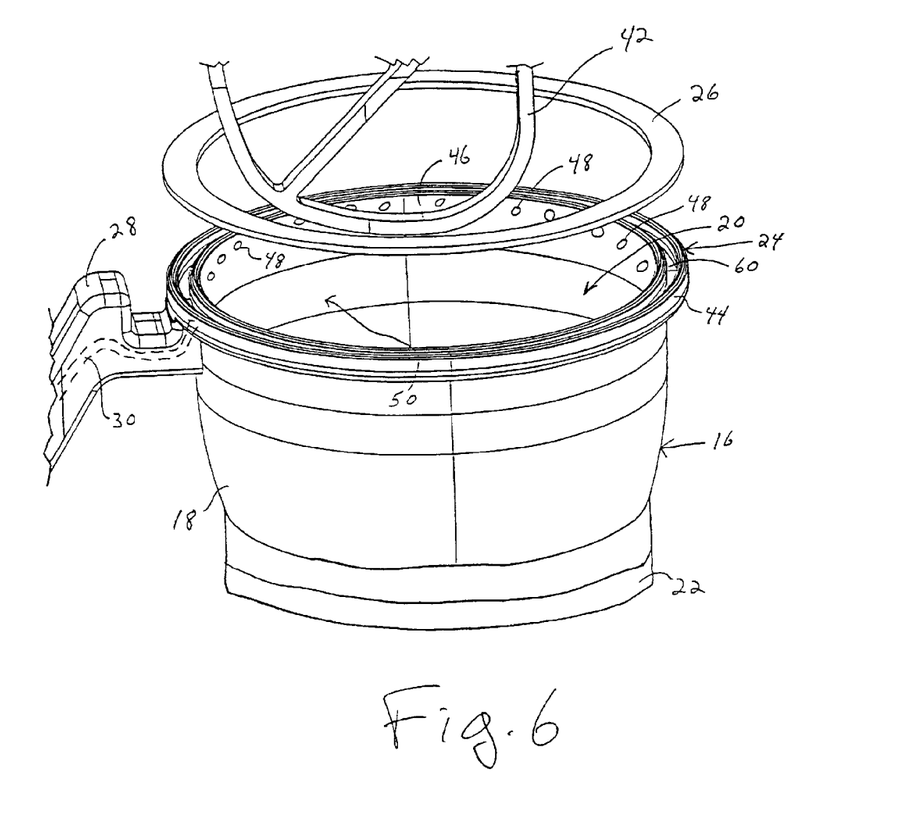
FIG. 6 is an enlarged perspective view of the bowl, vacuum seal and partial mixing blade of the exemplary bone cement mixing apparatus.
Figure 7:
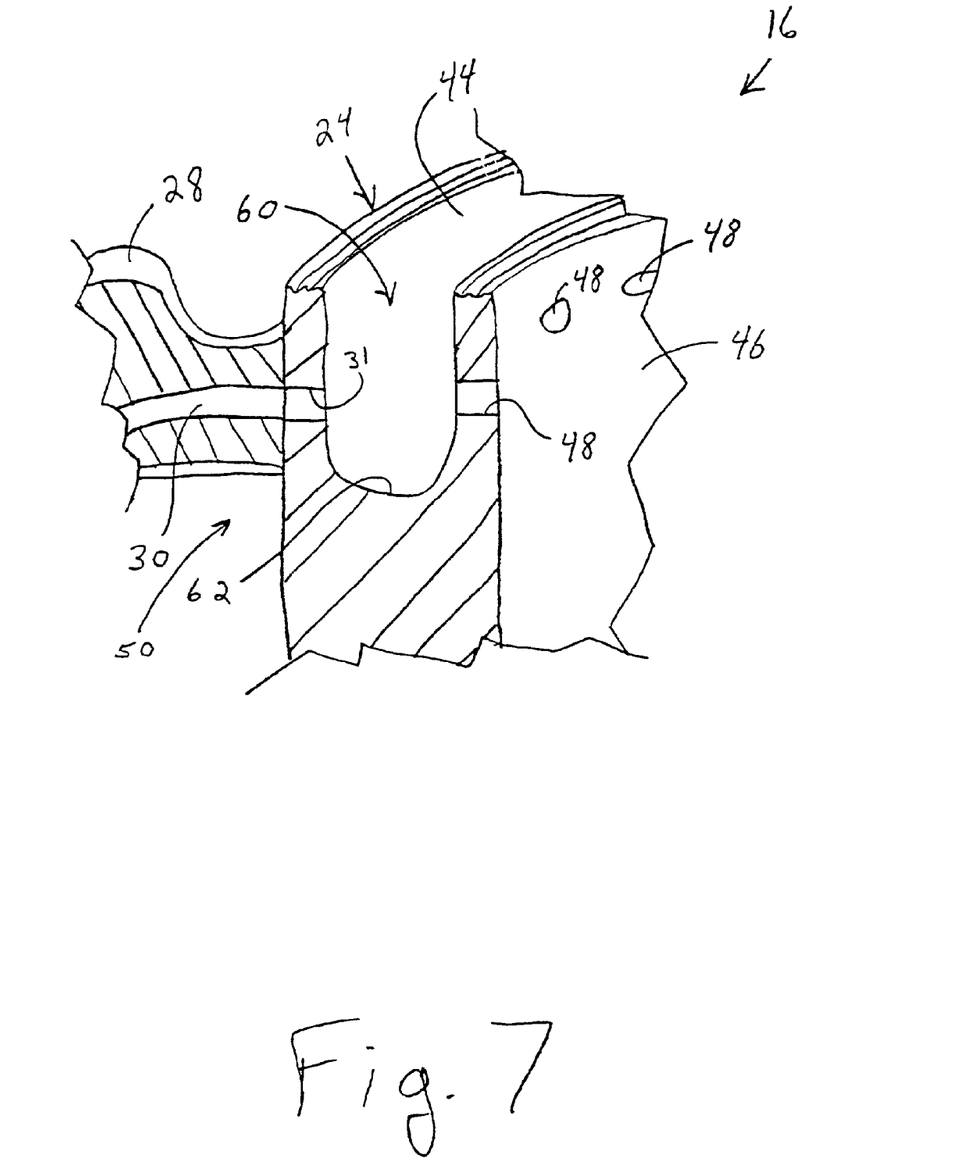
FIG. 7 is an enlarged sectional view of a portion of the bowl.

Referring to FIGS. 5, 6 and 7, the rim structure 24 and the vapor removal system 50 will be discussed. As indicated above, the rim structure 24 includes an outer wall 44 and an inner wall 46 that are space apart from each other. As such the outer wall 44 and the inner wall 46 define a cavity, channel, groove, or the like that together with a bottom wall 62 form a chamber 60. The chamber 60 extends annularly about the bowl 16 or the rim structure 24. The plurality of ports 48 that extend through the inner wall 46 provide communication between the interior 20 and the chamber 60. As best seen in FIG. 7, the tube 30 is in communication with the chamber 60. As particularly depicted in FIGS. 1 and 2, the tube 30 is in communication with the vacuum source 14. The seal 26 when placed on the rim structure 24 and over the chamber 60 provides a sealed chamber. Thus, any vacuum applied to the chamber 60 evacuates fumes or vapors from the interior 20 via the ports 48. Since the vapor removal system 50 is part of the bowl 16, evacuation of the interior 20 is accomplished even when the lid 32 is removed and the vacuum source 14 is creating a vacuum (suction).

The vapor removal system 50 includes the chamber 60 and the plurality of ports 48 (or alternatively, only one port 48) formed in the bowl 16 adjacent the chamber 60 and in communication therewith through inner wall 46, and the communication line (e.g. tube 30) that connects the chamber 60 with the vacuum source 14. In this manner, the interior 20 is in communication with the vacuum source 14.

Figure 3:
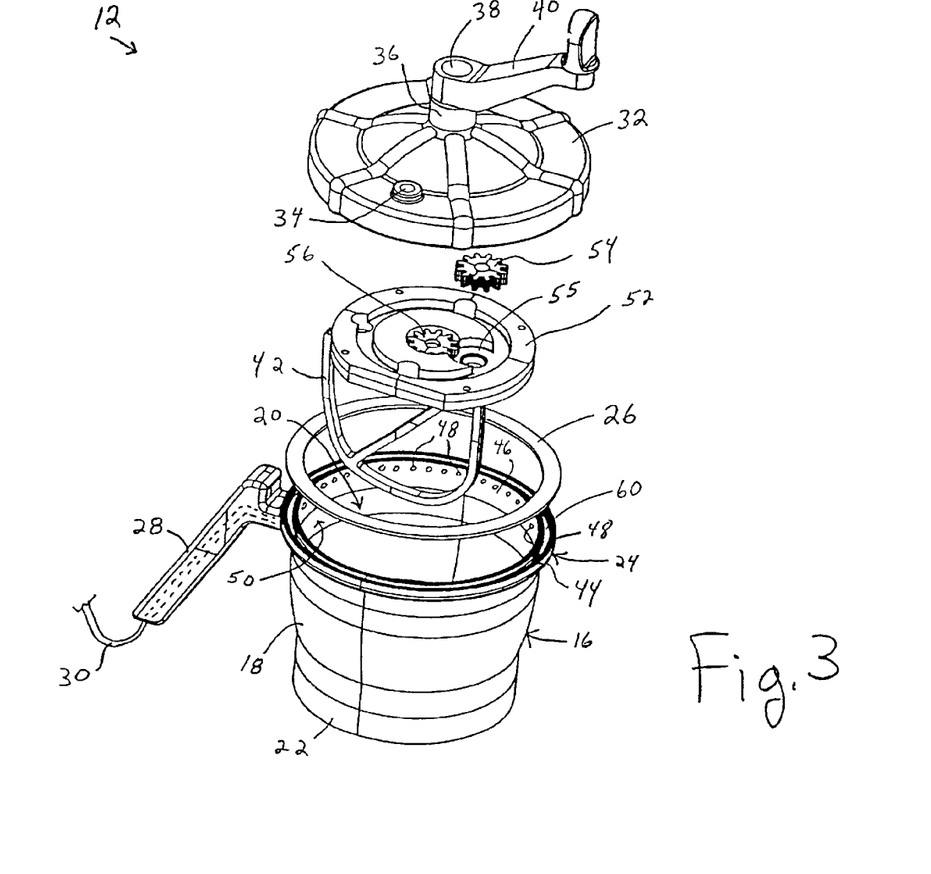
FIG. 3 is an exploded top perspective view of the exemplary bone cement mixing apparatus in accordance with the principles of the subject invention.
Figure 4:
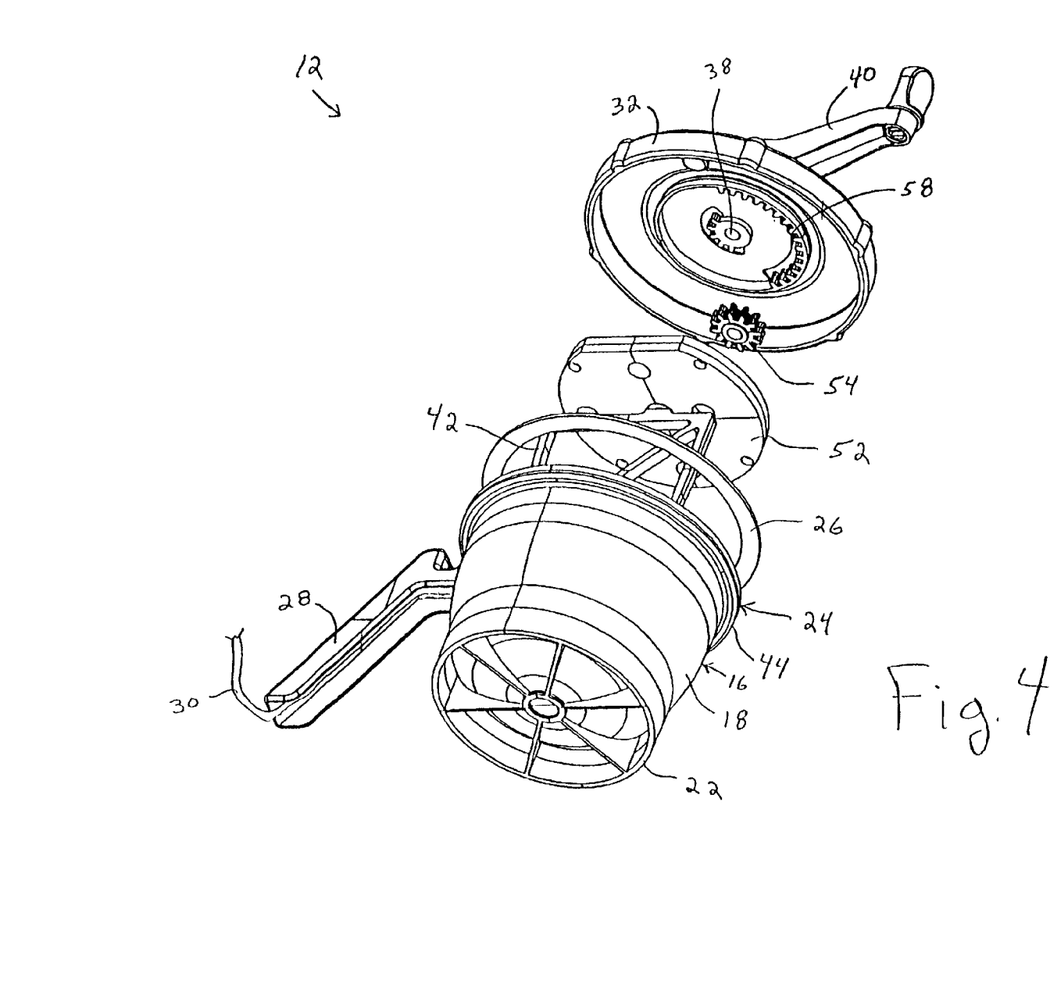
FIG. 4 is an exploded bottom perspective view of the exemplary bone cement mixing apparatus in accordance with the principles of the subject invention.

Referring now to FIGS. 3 and 4, the mixing apparatus 12 further includes a mixing blade 42 that depends from a support 52. The mixing blade 42 is configured, adapted and/or operative to rotate or revolve in both directions within the interior 20 and thus provide mixing of the monomers introduced therein. The mixing blade 42 has a shaft is in communication through the support 52 with a gear 56. The gear 56 is, in turn, in communication with a gear 54 that is adapted to be seated in the cutout 55. The gear 54 is adapted to be in communication with gear 58 and a gear 38 each disposed on an underside of the lid 32. Rotation of the crank 40 rotates the gearing to cause the mixing blade 42 to rotate. A detailed explanation of the present gearing arrangement for driving the mixing blade 42 is provided in U.S. patent application Ser. No. 10/002,045 which has been previously incorporated herein by reference. Reference should be made thereto for further explanation of the interface between the crank 40 and the mixing blade 42.

Use of the Subject Invention

A use and/or application of the subject invention will now be described. It should be appreciated, however, that the below-described use/application of the subject invention is only exemplary of one manner of use. Other manners of use not specifically described herein are contemplated. Referring to the figures, the seal 26 is seated on the rim structure 24 and over the chamber 60. The lid 32 is then locked down over the seal 26 and rim structure 24. The tube 30 is coupled to the vacuum source 14.

Either before or after introduction of the unmixed bone cement components into the bowl 16 via the inlet 34 in the lid 32, the vacuum source 14 is activated. Once the bone cement components have been introduced into the bowl 16, the crank 40 is turned to mix the bone cement components as appropriate for the particular bone cement components. During this time, fumes or vapors produced in the interior 20 of the bowl 16 are caused to be evacuated through the ports 48, into the chamber 60, into the tube 30 and into the vacuum source 14. Even after mixing is complete and the lid 32 has been removed, maintaining the vacuum source on will continue to remove remaining fumes from the bowl 16. The vacuum source may also remain on while the mixed bone cement is being removed from the bowl 16 for use by the surgeon.

There is a plurality of advantages of the subject invention arising from the various features of the bone cement mixing system described herein. One such advantage is that the vacuum tube line extends from the bowl rather than the lid. It will be noted that alternative embodiments of the bone cement mixing system of the subject invention may not include all of the features described yet still benefit from at least some of the advantages of such features. Those of ordinary skill in the art may readily devise their own implementations of a bone cement mixing system that incorporate one or more of the features of the subject invention and fall within the sprit and scope of the subject invention.

What is claimed is:

1. A bone cement mixing apparatus comprising:

a bowl defining an interior;

a lid detachably attachable to said bowl; and a bone cement vapor removal system formed in said bowl and operative to allow extraction of bone cement vapors or fumes from said interior, wherein said bone cement vapor removal system comprises: (i) a chamber formed proximate a top surface of said bowl, (ii) a plurality of inlet ports providing communication between said interior and said chamber, and (iii) an outlet port in communication with said chamber and configured to be coupled to a vacuum source, wherein said inlet ports are variable in size, and wherein said variable sized inlet ports comprises: (i) a first set of inlet ports of a first size proximate said outlet port; and (ii) a second set of inlet ports of a second size that is larger that said first size and disposed distal to said outlet port.

2. The bone cement mixing apparatus of claim 1, wherein said bone cement vapor removal system is operative to allow extraction after said lid has been detached from the bowl.

3. The bone cement mixing apparatus of claim 1, wherein said chamber is formed by a rim structure comprising:

an inner wall facing said interior;

an outer wall; and a bottom wall;

said inlet ports formed in said inner wall.

4. The bone cement mixing apparatus of claim 1, further comprising:

a handle extending from said bowl.

5. The bone cement mixing apparatus of claim 4, wherein said handle is formed integral with said bowl.

6. The bone cement mixing apparatus of claim 1, further comprising:

a bone cement component inlet formed in said lid.

7. A bone cement mixing apparatus comprising:

a bowl defining an interior;

a lid detachably attachable to said bowl; and a bone cement vapor removal system formed in said bowl and operative to allow extraction of bone cement vapors or fumes from said interior, wherein said bone cement vapor removal system comprises: (i) a chamber formed proximate a top surface of said bowl, (ii) a plurality of inlet ports providing communication between said interior and said chamber, and (iii) an outlet port in communication with said chamber and configured to be coupled to a vacuum source, wherein said inlet ports are variable in size, and wherein said variable sized inlet ports comprises graduated variability from a first size proximate said outlet port to a last size greater than said first size distal said outlet port.

8. A bone cement mixing apparatus comprising:

a bowl defining an interior;

an annular chamber formed in an upper annular rim of said bowl;

a plurality of inlet ports formed in said upper annular rim and providing communication between said interior of said bowl and said chamber;

a lid detachably attachable to said upper rim of said bowl;

an annular seal disposed on said upper rim; and an outlet port in communication with said chamber and configured to be coupled to a vacuum source, wherein said upper rim comprises: (i) an inner wall facing said interior, (ii) an outer wall, and (iii) a bottom wall, said inlet ports formed in said inner wall, wherein said inlet ports are variable in size, and wherein said variable sized inlet ports comprises: (i) a first set of inlet ports of a first size proximate said outlet port; and (ii) a second set of inlet ports of a second size that is larger that said first size and disposed distal to said outlet port.

9. The bone cement mixing apparatus of claim 8, further comprising:

a handle extending from said bowl.

10. The bone cement mixing apparatus of claim 9, wherein said handle is formed integral with said bowl.

11. The bone cement mixing apparatus of claim 9, wherein said outlet port is adjacent said handle.

12. The bone cement mixing apparatus of claim 11, further comprising a tube coupled to and in communication with said outlet port and the vacuum source, said tube extending through said handle.

13. The bone cement mixing apparatus of claim 8, further comprising:

a bone cement component inlet formed in said lid.

14. A bone cement mixing apparatus comprising:

a bowl defining an interior;

an annular chamber formed in an upper annular rim of said bowl;

a plurality of inlet ports formed in said upper annular rim and providing communication between said interior of said bowl and said chamber;

a lid detachably attachable to said upper rim of said bowl;

an annular seal disposed on said upper rim; and an outlet port in communication with said chamber and configured to be coupled to a vacuum source, wherein said upper rim comprises: (i) an inner wall facing said interior, (ii) an outer wall, and (iii) a bottom wall, said inlet ports formed in said inner wall, wherein said inlet ports are variable in size, and wherein said variable sized inlet ports comprises graduated variability from a first size proximate said outlet port to a last size greater than said first size distal said outlet port.

15. A bone cement mixing system comprising:

a vacuum source;

a mixing bowl device comprising:

a bowl defining an interior;

a lid detachably attachable to said bowl; and a bone cement vapor removal system formed in said bowl and operative to allow extraction of bone cement vapors or fumes from said interior when in communication with said vacuum source, wherein said bone cement vapor removal system comprises: (i) a chamber formed proximate a top surface of said bowl, (ii) a plurality of inlet ports providing communication between said interior and said chamber, and (iii) an outlet port in communication with said chamber and configured to be coupled to a vacuum source, wherein said inlet ports are variable in size, and wherein said variable sized inlet ports comprises: (i) a first set of inlet ports of a first size proximate said outlet port; and (ii) a second set of inlet ports of a second size that is larger that said first size and disposed distal to said outlet port.

16. The bone cement mixing system of claim 15, wherein said bone cement vapor removal system is operative to allow extraction after said lid has been detached from the bowl.

17. The bone cement mixing system of claim 15, wherein said chamber is formed by a rim structure comprising:

an inner wall facing said interior;

an outer wall; and a bottom wall;

said inlet ports formed in said inner wall.

18. The bone cement mixing system of claim 15, further comprising:

a handle extending from said bowl.

19. The bone cement mixing system of claim 18, wherein said handle is formed integral with said bowl.

20. The bone cement mixing system of claim 15, further comprising:

a bone cement component inlet formed in said lid.

21. The bone cement mixing system of claim 15, further comprising a tube providing communication between said vacuum source and said chamber.

22. A bone cement mixing system comprising:

a vacuum source;

a mixing bowl device comprising:

a bowl defining an interior;

a lid detachably attachable to said bowl; and a bone cement vapor removal system formed in said bowl and operative to allow extraction of bone cement vapors or fumes from said interior when in communication with said vacuum source, wherein said bone cement vapor removal system comprises: (i) a chamber formed proximate a top surface of said bowl, (ii) a plurality of inlet ports providing communication between said interior and said chamber, and (iii) an outlet port in communication with said chamber and configured to be coupled to a vacuum source, wherein said inlet ports are variable in size, and wherein said variable sized inlet ports comprises graduated variability from a first size proximate said outlet port to a last size greater than said first size distal said outlet port.

* * * * *